(12) United States Patent
Kurz et al.

(10) Patent No.: US 12,733,806 B2
(45) Date of Patent: Sep. 15, 2026

(54) EYE TESTING DEVICE

(71) Applicant: HEADS STOCKHOLM AB, Stockholm (SE)

(72) Inventors: Hans-Peter Kurz, Stockholm (SE); Bjorn A. Helland-Hansen, Ranheim (NO)

(73) Assignee: HEADS STOCKHOLM AB, Stockholm (SE)

( * ) Notice: Subject to any disclaimer, the term of this patent is extended or adjusted under 35 U.S.C. 154(b) by 197 days.

(21) Appl. No.: 18/294,632

(22) PCT Filed: Jul. 25, 2022

(86) PCT No.: PCT/SE2022/050727
§ 371 (c)(1),
(2) Date: Feb. 2, 2024

(87) PCT Pub. No.: WO2023/014265
PCT Pub. Date: Feb. 9, 2023

(65) Prior Publication Data

US 2024/0335111 A1 Oct. 10, 2024

(30) Foreign Application Priority Data

Aug. 2, 2021 (SE) .................................... 2150982-3

(51) Int. Cl.
*A61B 3/12* (2006.01)
*A61B 3/00* (2006.01)
*A61B 3/113* (2006.01)

(52) U.S. Cl.
CPC .............. *A61B 3/12* (2013.01); *A61B 3/0008* (2013.01); *A61B 3/0025* (2013.01);
(Continued)

(58) Field of Classification Search
CPC ....... A61B 3/12; A61B 3/0008; A61B 3/0025; A61B 3/0033; A61B 3/0041;
(Continued)

(56) References Cited

U.S. PATENT DOCUMENTS 7,494,222 B2 * 2/2009 Jackson ............... A61B 3/0041 351/224
9,492,081 B2 11/2016 Henry et al.
(Continued)

FOREIGN PATENT DOCUMENTS

AU 2017372951 A1 7/2019
JP 2011161122 A 8/2011
(Continued)

OTHER PUBLICATIONS

Supplementary report and Opinion from corresponding EP Application No. 22 85 3600, mailed May 30, 2025, all pages cited in its entirety.

(Continued)

*Primary Examiner* — William R Alexander
(74) *Attorney, Agent, or Firm* — Burr & Forman

(57) ABSTRACT

The present disclosure relates to a method and a corresponding device (1) for providing an eye metric. The device comprises a display unit (3), producing a visual stimulus (7) to an eye, a feedback unit (9) measuring a response to the stimulus, and an analysing unit (11), outputting a metric result. The device is configured to produce a recurring bleaching impulse together with the stimulus wherein the bleaching impulse is repeated with a frequency greater than 0.3 Hz. This serves to keep the cones of the eye's retina in a saturated state, and the produced metric may be useful in apparatuses for eye evaluation.

13 Claims, 2 Drawing Sheets

(52) U.S. Cl.
CPC .......... *A61B 3/0033* (2013.01); *A61B 3/0041* (2013.01); *A61B 3/0091* (2013.01); *A61B 3/113* (2013.01)

(58) Field of Classification Search
CPC ....... A61B 3/0091; A61B 3/113; A61B 3/022; A61B 3/028; A61B 3/032; A61B 3/063; A61B 5/0059
USPC .................................................. 351/205, 211
See application file for complete search history.

(56) References Cited

U.S. PATENT DOCUMENTS

| | | | | |
|---|---|---|---|---|
| 10,542,882 | B2 * | 1/2020 | Lichtenauer | A61B 3/024 |
| 2004/0087843 | A1 | 5/2004 | Rice et al. | |
| 2007/0121071 | A1 * | 5/2007 | Jackson | A61B 3/0025 351/246 |
| 2016/0213301 | A1 | 7/2016 | Port | |
| 2017/0325676 | A1 * | 11/2017 | Lichtenauer | A61B 3/024 |
| 2019/0269322 | A1 * | 9/2019 | Todd | A61B 3/152 |
| 2020/0093361 | A1 * | 3/2020 | Jackson | G08B 21/182 |
| 2020/0221945 | A1 * | 7/2020 | Kelly | G16H 50/20 |
| 2020/0352434 | A1 * | 11/2020 | Edwards | A61B 3/0033 |
| 2020/0397281 | A1 | 12/2020 | Pundlik et al. | |
| 2021/0307601 | A1 * | 10/2021 | Edwards | A61B 3/0033 |

FOREIGN PATENT DOCUMENTS

| | | | |
|---|---|---|---|
| JP | 2013534165 | A | 9/2013 |
| JP | 2020500640 | A | 1/2020 |
| WO | 2016081978 | A1 | 6/2016 |
| WO | 2019165263 | A1 | 8/2019 |
| WO | 2020061546 | A1 | 3/2020 |

OTHER PUBLICATIONS

International Search Report and Written Opinion of International Application No. PCT/SE2022/050727 mailed Sep. 15, 2022, all pages cited in its entirety.

Notice of Reasons for Refusal from corresponding Japanese Application No. 2024-506184, mailed Jun. 2, 2026, all pages cited in its entirety.

* cited by examiner 3
5
7
13
9
17
1
11

19

25
23
7
21

EYE TESTING DEVICE

FIELD OF THE INVENTION

The present disclosure relates to a device for providing an eye metric. The device comprises a display unit, producing a visual stimulus to an eye, a feedback unit measuring a response to the stimulus and an analysing unit, outputting a metric result.

BACKGROUND OF THE INVENTION

Such devices can be used to detect different retina conditions of a tested person, such as, for instance, age-related macular degeneration, AMD. Such pathologies can often be detected in other ways such as for instance by fundus photography. Another method is to measure dark adaptation of the eye such as disclosed in WO-2005/023094-A2, where the dark adaptation of retina rods is used to determine whether a tested person has a progressing AMD condition such that therapy can be introduced at an early stage of the progress of the condition.

One problem with such method is that they are quite slow. A test may at best take 20 minutes or more in many cases. The efficiency of the test is therefore relatively low.

SUMMARY OF THE INVENTION

One object of the present disclosure is therefore to provide a quicker testing device such that more patients can be tested during a given time frame. This object is achieved by means of a device as defined in claim 1. More particularly, the device is then configured to produce a recurring bleaching impulse together with the stimulus. Then, the bleaching impulse is repeated with a frequency greater than 0.3 Hz.

Any bleached area of the retina, cones or rods, can be tested under photopic, i.e. daylight-like, conditions. For instance, when after the bleach the stimuli is shown onto the fovea, primarily cones are tested. When on the other hand the stimuli are projected onto the peripheral visual field, primarily rods are tested.

While cones may be connected to central vision-related pathologies such as AMD in a different way than rods, cones are also very dominant by numbers in the macula of the eye and representative of the macula's capability. Therefore, also the cones dark adaptation can be used to detect early stages of AMD or other central vision-related pathologies and with much shorter testing time needed as compared to prior dark adaptation testing methods. Hence the testing procedure becomes very efficient.

The feedback unit may comprise an eye-tracking unit, measuring the eye's movements in response to said stimulus. This provides more objective feedback than for instance the tested person using a button or a hand control to provide feedback as cheating becomes virtually impossible. However, for a simple arrangement, or for updating a legacy system with the bleaching functionality, a manual control such as a button, hand control or joystick may be considered for recording a tested person's response to the stimulus.

The display unit may be configured to produce a moving stimulus with a decreasing visibility parameter, meaning that it becomes increasingly more difficult for the tested person to follow the stimulus, for instance a moving symbol. The eye-tracking unit may be configured to detect the eye following and subsequently losing visual contact with the stimulus symbol. The analysing unit may then be configured to provide a metric result based on the visibility parameter at the time when loss of visual contact was detected. This gives an objective measurement of the tested eye's acuity. The varied visibility parameter may be for instance size, contrast (colour or grey-scale), brightness, and movement velocity.

The stimulus may be a symbol that moves continuously, and additionally or alternatively may make jumps so as to test also peripheral vision. Specifically, the display unit may be configured to produce a stimulus in the form of a symbol that carries out a sequence of jumps, and an eye-tracking unit, for instance, may be configured to detect whether the eye is capable of following the stimulus, and the analysing unit is configured to provide a metric result based on characteristics of the symbol and/or the jump at the time in the sequence when loss of visual contact was detected. In general, continuous movements test central vision and jumping movements more peripheral vision.

As an alternative to the varying of the stimulus visibility parameter, the display unit may be configured to produce a moving stimulus, and the frequency with which the bleaching impulse is repeated may increase until the tested person is no longer capable of following the stimulus symbol, for instance. The eye-tracking unit can detect the eye following and subsequently loosing visual contact with the stimulus, and the analysing unit can provide a metric result based on the bleaching frequency at the time when loss of visual contact was detected. Those alternatives may also be combined.

The bleaching impulse may exceed 40 cd/m$^2$ at the location of the eye, and the bleaching impulse may last up to 1 second depending on the repeat frequency. Typically, however, the bleaching pulse lasts 10% or less of a bleaching impulse period time.

The bleaching impulse is produced by the display device, such as an OLED display, however, it is also possible to use a light source separate from the display device.

The bleaching impulse may typically be repeated with a frequency in the range 0.5-20 Hz.

A corresponding method is also considered.

DETAILED DESCRIPTION OF THE EXEMPLARY EMBODIMENTS

Figures 1A, 1B, 2:
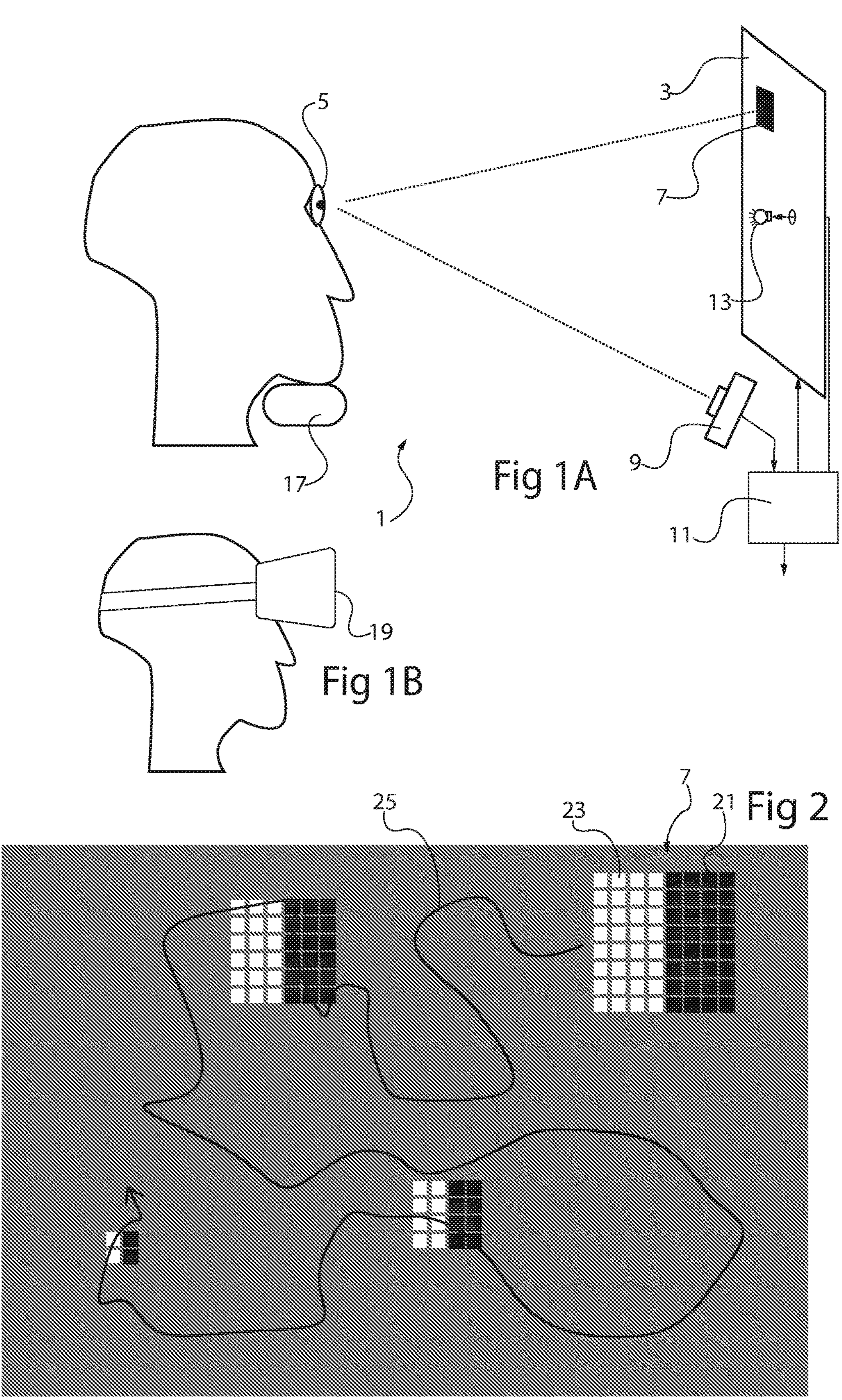
FIG. 1A schematically illustrates a basic arrangement for carrying out tests.
FIG. 1B illustrates the features of FIG. 1A included in a goggle's arrangement.
FIG. 2 shows an example of a stimulus used for testing.

The present disclosure relates in general to devices for providing an eye metric. The device is primarily intended for detecting diseases that impact central areas of the retina, for instance glaucoma, age-related macular degeneration (AMD or ARMD, hereinafter AMD) or diabetic retinopathy. However, other conditions may also be detected or distinguished between by means of the devices disclosed herein. The device is particularly useful for detecting AMD at an early stage of the progression of the condition.

AMD is a common condition in ageing populations. While the condition is relatively rare before the age of 60, it is estimated to affect more than 10% of the population over the age of 80. Generally, the macula in the centre of the retina is affected which eventually may result in lost central vision, which can make activities such as driving, reading and computer usage more or less impossible.

Two types of AMD exist, dry- and wet-, which have different characteristics and can arise independently of each other. It is believed that the more slowly progressing dry AMD, which at present cannot be treated, in some cases can transition into the more quickly progressing wet form. For the wet form, some therapies exist although they need to be introduced as soon as possible to be able to attenuate the progression of the condition in a meaningful way. Therefore, early detection of AMD is important.

One possible method for detection is the photostress test. Then, an eye is bleached for about 10 seconds, and it is measured the recovery time a patient needs to read normally from a Snellen chart. This usually only offers a subjective result. Patients can fake the result and the results are depending on the patient's self-confidence to read uncertain values. One patient might wait significantly longer before reading a character compared to a more confident patient who takes a higher risk of reading an incorrect character.

There are different ways for detecting AMD, typically using fundus photography and usual eye testing procedures such as Snellen charts. For early-stage detection however, dark adaptation measurements have been found to be most useful. One example of a dark adaptation measurement is shown in WO-2005/023094-A2 where a test subject's eye is exposed to a bleaching light pulse, meaning a light that saturates the photoreceptor cells, cones and rods, of the retina. Then it is determined, by subsequently providing a stimulus in a much darker condition to the subject and recording a response thereto, a series of dark adaptation measurements as the eye recovers from the bleaching pulse. The eye's capability of adapting to the dark condition subsequent to the bleaching pulse is highly affected by an early-stage AMD condition. The above document is mainly concerned with scotopic (very dark conditions) vision capabilities that is mainly provided the retina rods. As those cells are very sensitive to light and are said to be able to register a single photon, they recover very slowly from a bleaching impulse. For this reason, a test of this kind can be very time-consuming, 10-20 minutes being considered typical.

The present disclosure takes a different approach that allows a much quicker testing sequence, while still allowing early detection of AMD. The present disclosure provides, as schematically outlined in FIG. 1A, an eye testing device 1 comprising a display unit 3, producing a visual stimulus 7 to an eye 5 of a person being tested. There is provided a feedback unit 9 measuring an eye response to the stimulus. An analysing unit 11, which may also function as a controller, analyses the response in relation to the stimulus typically to determine the acuity of the eye, and outputs a metric result, which may be used for a subsequent diagnostic evaluation. A chin rest 17 may be provided to keep the tested person's head still.

The device 1 in FIG. 1A is configured to produce bleaching impulses towards the eye under evaluation together with the stimulus using a bleaching unit 13. The bleaching unit 13 may be mounted at any location where it is able to shine upon the retina, typically primarily on the macula, but also on other locations of the retina. This means that the eye will operate in a bleached state. The bleaching impulse is recurring, being repeated with a frequency typically greater than 0.3 Hz. This means that the scotopic dark adaptation of the rods will to some extent be disabled during the measurement. This is in contrast to previous systems relying mainly on retina rods data during scotopic conditions. As will be discussed, a useful analysis can still be made by comparing the data achieved in this way with reference data. As shown in FIG. 1B, some or all of the units of the more stationary system of FIG. 1A can be included in a virtual reality, VR-, goggles type arrangement for a more portable system 1'.

The display unit 3 of FIG. 1A may be any type of display capable of displaying visual stimuli. Typically, the display unit 3 may be an LCD, LED, microLED or OLED display, used to show moving stimuli with changing visibility as will be shown, but other forms of display units, even a legacy type Snellen chart could be used or screens where individual dots may be lit in different locations. Typically, one eye at a time is tested even if it would be possible to test both eyes simultaneously. It is possible also to test one eye with the other eye covered or the other eye used to decrease pupil size to a desired diameter.

In one example, see FIG. 1B, the display unit is included in a VR headset setup 19 worn by the person being tested, although stationary displays are useful as well.

The feedback unit 9 measuring a response to the stimulus can be accomplished in many different ways. In one example illustrated in FIG. 1A, an eye-tracking apparatus 9 is used that directly measures the eyes' response to a stimulus. However, simpler forms of feedback units are possible, such as for instance a push-button that the tested person presses when a stimulus appears on a screen or for instance a joystick that can be used to indicate a displayed stimulus location in relation to a reference point, or to indicate the orientation of a sequence of arrows, with decreasing size or contrast, displayed on a screen, for instance. In general, any feedback unit can be used that provides quick and objective feedback data from which it can be determined whether the tested person can see the stimulus or can see the stimulus with a predetermined resolution. Using eye tracking is preferred as it prevents cheating to a great extent.

The analysing unit and controller 11 determines, based on the data from the feedback unit and in relation to the stimulus 7 presented on the display device 3, a metric of the eye's performance under influence of bleaching pulses. Typically, a metric related to the acuity or contrast sensitivity of the eye is determined in this way. This metric may then be used for a subsequent diagnostic evaluation of the eye. Some useful information may be obtained from the metric itself, for instance by comparing the metric to a metric obtained in the same way at a previous session, perhaps several months before, then giving an indication of whether there is a progressing retinal condition such as for instance AMD or diabetic retinopathy.

However, it is considered advantageous to compare the data with bleached or non-bleached reference data. That data may be obtained from a number of reference test persons without any AMD condition, for instance as determined with optical coherence tomography, OCT, or fundus photography. Another option, as will be shown, is to first carry out a test on the same test person without inducing a bleached condition. Then, the same test is carried out with bleaching turned on, and the difference between the results of the two tests are used for evaluation.

The bleaching light may, as illustrated in FIG. 1A, be provided by means of a separate light source 13, as indicated, but in many cases the display itself is capable of producing a light flow with a bleaching intensity. The bleaching light may also be provided via semi-transparent mirrors located in between the display device and the person to be tested.

Typically, a bleaching intensity of more than 40 cd/$m^2$, but more specifically in a preferred range from 40-4000 cd/$m^2$ towards the tested eye.

The bleaching unit 13 may be controlled by the analysing unit/controller 11, which may for instance vary the intensity repeating frequency and duration of the bleaching pulses. Typically, a bleaching pulse is shorter than 1 second, but may be considerably shorter depending on the bleaching frequency, i.e. bleaching repetition rate, used. This frequency may vary between 0.3 Hz and 20 Hz, typically more than 0.5 Hz. The bleaching pulse lasts usually 10% or less of the period time corresponding to the inverse of the bleaching frequency. Different bleaching wavelengths may be used, but typically within the range of 420-580 nm to influence the different types of cones in the retina.

The visual stimulus may be produced in different ways depending on the intended way of providing feedback. In its simplest form, different symbols may be produced for instance with decreasing size and/or contrast, and the tested person is instructed to read out loud the sequence which is input by an operator or compared to a sequence chart by an operator. In any case, it can be determined by the analysing unit at which size and/or contrast the tested person fails with identifying the displayed stimulus. As mentioned, it would also be possible for instance to display a random sequence of arrows up/down/right/left and let the tested person input a corresponding sequence with a joystick. The analysing unit detects when the tested person fails.

FIG. 2 illustrates one suitable way of producing a visual stimulus on a display device for feedback using an eye tracking unit. In this case, a symbol 7 moves over the screen while its size or the contrast compared to the background, for instance, decreases, either continuously or stepwise. As illustrated, the symbol may comprise two or more black 21 and white 23 fields, and the average brightness of the symbol may be substantially the same as the brightness of the background. The symbol may thus shrink, or alternatively, the black and white fields slowly progress towards grey such that the symbol gradually blends in more with the background. As yet another alternative, the fields of the symbol may be divided into subfields, such that a black and each white field becomes two black and two white fields, for instance. The symbol becomes progressively less visible regardless of the method chosen. In general, a visibility parameter is decreased.

The symbol 7 may move in a pattern 25 that the tested person perceives as random, such that he or she cannot predict the coming movements of the symbol. While the symbol 7 moves, an eye tracking function 9, cf. FIG. 1A evaluates how the eye follows the symbol. When the tested person finally loses track of the symbol e.g., due to low contrast, this can be readily detected as the correlation between the symbol's and the eye's movement breaks down. With knowledge of the state of the symbol at the time when the tested person loses track of the symbol gives an estimate of the acuity of the tested person's eye.

As an alternative, or in combination therewith, it would be possible to increase the bleaching frequency until the tested person loses track of the symbol/stimulus 7 due to the saturation of the retina. This is detected by the eye tracking unit 9, and the analysing unit 11 provides a metric based on the bleaching frequency at the time of loss of track. This can be done with a constant symbol, a varying symbol or a symbol that is varied in between test cycles. The precision of the produced metric may be improved in this way.

A stimulus in the form of a symbol 7 that moves continuously over the display device will primarily test the central vision, as a smooth pursuit approach is used. It is possible to carry out some testing of peripheral vision by letting the stimulus jump or, more generally, to move in a non-continuous fashion. If the symbol jumps in a direction that the tested person cannot predict, the tested person's peripheral vision in the sector in question is tested in a bleached condition. This means that central and peripheral vision can be tested in the same process. In addition other ways of decreasing a visibility parameter as described above, is possible to increase the jump size.

Figure 3:
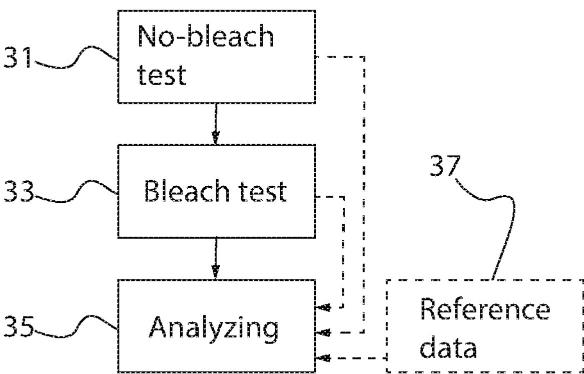
FIG. 3 illustrates a flow chart for a testing sequence.

FIG. 3 illustrates a flow chart for a testing sequence. In a first step 31, which is optional, the tested person's acuity is tested without producing any bleaching impulses. This may be done to obtain reference information for later use and may be carried out for instance as indicated in FIG. 2.

In a second step 33, an identical or similar test is carried out where additionally the bleaching unit 13 is active producing a light flow wholly or partly saturating retinal cells repeatedly while the display device 3 produces stimuli 7 and the feedback unit registers a response thereto.

In a third step 35, the result produced in the second step 33 is analysed. This can be done by comparing this result with the result produced as a reference in the optional first step 31 or comparing with reference data 37 which may be saved from other testing persons or from previous tests of the currently tested person. Those different reference sources may also be combined. The result of the third step is a retinal metric under bleached conditions which may be used for subsequent diagnostic purposes.

The present disclosure is not restricted to the above disclosed examples and may be varied and altered in different ways within the scope of the appended claims.

The invention claimed is:

1. A device for providing an eye metric, the device comprising a display unit, producing a visual stimulus to an eye, a feedback unit measuring a response to the stimulus and an analysing unit, outputting a metric result, characterized by the device being configured to produce a recurring bleaching impulse together with the stimulus wherein the bleaching impulse is repeated with a frequency greater than 0.3 Hz, wherein the display unit is configured to produce a moving stimulus, the frequency with which the bleaching impulse is repeated increases, the eye-tracking unit is configured to detect the eye following and subsequently loosing visual contact with the stimulus, and the analysing unit is configured to provide a metric result based on the bleaching frequency at the time when loss of visual contact was detected.

2. The device according to claim 1, wherein the feedback unit comprises an eye-tracking unit, measuring the eye's movements in response to said stimulus.

3. The device according to claim 1, wherein the feedback unit comprises a manual control, recording a tested person's response to said stimulus.

4. The device according to claim 2, wherein the display unit is configured to produce a moving stimulus with a decreasing visibility parameter, the eye-tracking unit is configured to detect the eye following and subsequently loosing visual contact with the stimulus, and the analysing unit is configured to provide a metric result based on the visibility parameter at the time when loss of visual contact was detected.

5. The device according to claim 1, wherein the display unit is configured to produce a stimulus that carries out a sequence of jumps, the eye-tracking unit is configured to detect whether the eye is capable of following the stimulus, and the analysing unit is configured to provide a metric result based on characteristics of the symbol and/or the jump at the time in the sequence when loss of visual contact was detected.

6. The device according to claim 4, wherein the visibility parameter is a parameter in the group comprising size, grey contrast, colour contrast brightness, and movement velocity and jump size.

7. The device according to claim 1, wherein the bleaching impulse exceeds 40 cd/$m^2$ at the location of the eye.

8. The device according to claim 7, wherein the bleaching impulse lasts up to 1 second.

9. The device according to claim 8, wherein the bleaching pulse lasts 10% or less of a bleaching pulse period time.

10. The device according to claim 1, wherein the bleaching impulse is produced by the display device.

11. The device according to claim 1, wherein the bleaching impulse is produced by a light source separate from the display device.

12. The device according to claim 1, wherein the bleaching impulse is repeated with a frequency in the range than 0.5-20 Hz.

13. A method for providing an eye metric in a device comprising a display unit, producing a visual stimulus to an eye, a feedback unit measuring a response to the stimulus, and an analysing unit, outputting a metric result, characterized by a recurring bleaching impulse is produced together with the stimulus wherein the bleaching impulse is repeated with a frequency greater than 0.3 Hz, wherein the display unit is configured to produce a moving stimulus, the frequency with which the bleaching impulse is repeated increases, the eye-tracking unit is configured to detect the eye following and subsequently loosing visual contact with the stimulus, and the analysing unit is configured to provide a metric result based on the bleaching frequency at the time when loss of visual contact was detected.

* * * * *